United States Patent
Xu

(10) Patent No.: US 12,427,198 B2
(45) Date of Patent: Sep. 30, 2025

(54) CARRIER-FREE CURCUMIN NANOPARTICLES FOR EGFR-POSITIVE CANCER THERAPY

(71) Applicant: UNIVERSITY OF SOUTH CAROLINA, Columbia, SC (US)

(72) Inventor: Peisheng Xu, Columbia, SC (US)

(73) Assignee: UNIVERSITY OF SOUTH CAROLINA, Columbia, SC (US)

( * ) Notice: Subject to any disclaimer, the term of this patent is extended or adjusted under 35 U.S.C. 154(b) by 7 days.

(21) Appl. No.: 18/409,042

(22) Filed: Jan. 10, 2024

(65) Prior Publication Data

US 2024/0148881 A1    May 9, 2024

Related U.S. Application Data

(63) Continuation-in-part of application No. 17/213,750, filed on Mar. 26, 2021, now Pat. No. 11,904,022.

(60) Provisional application No. 63/029,782, filed on May 26, 2020.

(51) Int. Cl.
| | |
|---|---|
| *A61K 47/55* | (2017.01) |
| *A61K 9/14* | (2006.01) |
| *A61K 47/60* | (2017.01) |
| *A61P 35/00* | (2006.01) |

(52) U.S. Cl.
CPC ............ *A61K 47/55* (2017.08); *A61K 9/14* (2013.01); *A61K 47/60* (2017.08); *A61P 35/00* (2018.01)

(58) Field of Classification Search
CPC .. A61K 31/12; A61K 31/517; A61K 2300/00; A61K 47/6935; A61K 47/54; A61K 47/60; A61K 9/5123; A61K 9/5146; A61K 9/5192
See application file for complete search history.

(56) References Cited

PUBLICATIONS

Cheng et al., "Carrier-Free Nanoassembly of Curcumin-Erlotinib Conjugate for Cancer Targeted Therapy," Advanced Healthcare Materials, vol. 9, No. 19 (Oct. 7, 2020).
Gao et al., "Erlotinib-Guided Self-Assembled Trifunctional Click Nanotheranostics for Distinguishing Druggable Mutations and Synergistic Therapy of Nonsmall Cell Lung Cancer," Mol. Pharmaceutics Nov. 15, 2018, 5146-5161.
Chen et al., "Curcumin based combination therapy for anti-breast cancer: from in vitro drug screening to in vivo efficacy evaluation," Front. Chem. Sci. Eng. 10, 383-388 (2016). Https://doi.org/10.1007/s11705-016-1574-2.
Yamauchi et al., "Coadministration of Erlotinib and Curcumin Augmentatively Reduces Cell Viability in Lung Cancer Cells," Phytotherapy Research, vol. 28, No. 5 (May 2014), pp. 728-735.
Ja Vadi et al., "Curcumin mediated down-regulation of αV β3 integrin and up-regulation of pyruvate dehydrogenase kinase 4 (PDK4) in Erlotinib resistant SW480 colon cancer cells," Phytotherapy Research, vol. 32, No. 2, pp. 355-364 (Feb. 2018).

*Primary Examiner* — Alicia L Otton
(74) *Attorney, Agent, or Firm* — DORITY & MANNING, P.A.

(57) ABSTRACT

A carrier-free nanoparticle based on the self-assembly of curcumin-erlotinib conjugate (EPC) that exhibits stronger cell killing, better anti-migration effects, and anti-invasion effects for pancreatic cancer cells than the combination of free curcumin and erlotinib.

14 Claims, 12 Drawing Sheets

CARRIER-FREE CURCUMIN NANOPARTICLES FOR EGFR-POSITIVE CANCER THERAPY

CROSS REFERENCE TO RELATED APPLICATION

This application is a Continuation Application of U.S. patent application Ser. No. 17/213,750, having a filing date of Mar. 26, 2021, which claims filing benefit of U.S. Provisional Patent Application Ser. No. 63/029,782, having a filing date of May 26, 2020, both of which are incorporated herein by reference for all purposes.

STATEMENT REGARDING FEDERALLY SPONSORED RESEARCH

This disclosure was made with government support under R15 CA188847 by the National Institute of Health. The government has certain rights in the invention.

TECHNICAL FIELD

The present disclosure relates to a carrier-free nanoparticle based on the self-assembly of curcumin-erlotinib conjugate (EPC) that exhibits stronger cell killing, better anti-migration effects, and anti-invasion effects for pancreatic cancer cells than the combination of free curcumin and erlotinib.

BACKGROUND

Epithelial cell cancers, for example, prostate cancer, breast cancer, colon cancer, lung cancer, pancreatic cancer, ovarian cancer, cancer of the spleen, testicular cancer, cancer of the thymus, etc., are diseases characterized by abnormal, accelerated growth of epithelial cells. This accelerated growth initially causes a tumor to form. Eventually, metastasis to different organ sites can also occur. Although progress has been made in the diagnosis and treatment of various cancers, these diseases still result in significant mortality.

Epidermal growth factor receptor (EGFR) is a 170 kilodalton (kDa) membrane-bound protein expressed on the surface of epithelial cells. EGFR is a member of the growth factor receptor family of protein tyrosine kinases, a class of cell cycle regulatory molecules. (W. J. Gullick et al., 1986, Cancer Res., 46:285-292). EGFR is activated when its ligand (either EGF or TGF-α) binds to the extracellular domain, resulting in autophosphorylation of the receptor's intracellular tyrosine kinase domain (S. Cohen et al., 1980, J. Biol. Chem., 255:4834-4842; A. B. Schreiber et al., 1983, J. Biol. Chem., 258:846-853).

EGFR is the protein product of a growth promoting oncogene, erbB or ErbB1, that is but one member of a family, i.e., the ERBB family of protooncogenes, believed to play pivotal roles in the development and progression of many human cancers. In particular, increased expression of EGFR has been observed in breast, bladder, lung, head, neck and stomach cancer as well as glioblastomas. The ERBB family of oncogenes encodes four structurally related transmembrane receptors, namely, EGFR, HER-2/neu (erbB2), HER-3 (erbB3) and HER-4 (erbB4). Clinically, ERBB oncogene amplification and/or receptor overexpression in tumors have been reported to correlate with disease recurrence and poor patient prognosis, as well as with responsiveness in therapy. (L. Harris et al., 1999, Int. J. Biol. Markers, 14:8-15; and J. Mendelsohn and J. Baselga, 2000, Oncogene, 19:6550-6565).

EGFR is composed of three principal domains, namely, the extracellular domain (ECD), which is glycosylated and contains the ligand-binding pocket with two cysteine-rich regions; a short transmembrane domain, and an intracellular domain that has intrinsic tyrosine kinase activity. The transmembrane region joins the ligand-binding domain to the intracellular domain. Amino acid and DNA sequence analysis, as well as studies of nonglycosylated forms of EGFR, indicate that the protein backbone of EGFR has a mass of 132 kDa, with 1186 amino acid residues (A. L. Ullrich et al., 1984, Nature, 307:418-425; J. Downward et al., 1984, Nature, 307:521-527; C. R: Carlin et al., 1986, Mol. Cell. Biol., 6:257-264; and F. L. V. Mayes and M. D. Waterfield, 1984, The EMBO J., 3:531-537).

The binding of EGF or TGF-α to EGFR activates a signal transduction pathway and results in cell proliferation. The dimerization, conformational changes and internalization of EGFR molecules function to transmit intracellular signals leading to cell growth regulation (G. Carpenter and S. Cohen, 1979, Ann. Rev. Biochem., 48:193-216). Genetic alterations that affect the regulation of growth factor receptor function, or lead to overexpression of receptor and/or ligand, result in cell proliferation. In addition, EGFR has been determined to play a role in cell differentiation, enhancement of cell motility, protein secretion, neovascularization, invasion, metastasis and resistance of cancer cells to chemotherapeutic agents and radiation. (M.-J. Oh et al., 2000, Clin. Cancer Res., 6:4760-4763).

A variety of inhibitors of EGFR have been identified, including a number already undergoing clinical trials for treatment of various cancers. For a recent summary, see de Bono, J. S. and Rowinsky, E. K. (2002), "The ErbB Receptor Family: A Therapeutic Target For Cancer", Trends in Molecular Medicine, 8, S 19-26.

Anti-cancer drug loaded nanoparticles have been explored extensively to decrease side effects while improving their therapeutic efficacy. Most nanoparticle based drug delivery systems are composed of a carrier and a payload. However, due to the low drug loading content, premature drug release, non-standardized or non-uniform carrier structure, and difficulty in predicating the fate of the carrier, only a few nanomedicines have been approved by FDA.

Accordingly, it is an object of the present disclosure to provide an improved nanoparticle with improved migration and invasion effects.

Citation or identification of any document in this application is not an admission that such a document is available as prior art to the present disclosure.

SUMMARY

Disclosed herein is a carrier-free nanoparticle based on the self-assembly of curcumin-erlotinib conjugate (EPC), which has a size of about 146.3 nm with a PDI of 0.157. The EPC nanoparticle exhibited stronger cell killing, better anti-migration and anti-invasion effects for BxPC-3 pancreatic cancer cells than the combination of free curcumin and erlotinib. Furthermore, EPC nanoparticle could effectively accumulate in the tumor tissue in a xenograft tumor mouse model. Consequently, EPC nanoparticles effectively reduced the growth of pancreatic tumor and extended the medium survival time of the tumor-bearing mice from 22 days to 68 days. In addition, no systemic toxicity was detected in the major organs from the mice receiving EPC treatment. Attributed to the uniformity of the curcumin-erlotinib conjugate and easiness of scaling up. EPC could be translated into power tool in fighting against pancreatic cancer.

The above objectives are accomplished according to the present disclosure by providing in a first embodiment, a method for preparing a carrier-free nanoparticle for tumor growth inhibition. The method may include synthesizing polyethylene glycol (PEG) modified erlotinib, conjugating the PEG modified erlotinib with curcumin to form an erlotinib-curcumin conjugate, dissolving the erlotinib-curcumin conjugate in acetone to form a solution, and adding the solution dropwise to deionized water to self-assemble at least one nanoparticle. Further, the at least one nanoparticle may be administered to a cancer cell. Still, the cancer cell may be a pancreatic cancer cell. Further yet, the cancer cell is a human pancreatic cancer cell. Again, the nanoparticle may be delivered in a dose of at least 10 mg/kg into a subject. Further, the nanoparticle may be offered at a dose of 1 mg/kg, 2, 3, 4, 5, 6, 7, 8, 9, 10, 15, 20, 25, 30, 35, 40, 45, 50, or 55 mg/kg as well as ranges of these amounts. Still yet, introduction of the at least one nanoparticle may reduce cancer cell viability. Moreover, introduction of the at least one nanoparticle may slow tumor volume growth profiles.

In a further embodiment, a method for inhibiting tumor growth is provided. The method may include introducing a carrier-free nanoparticle to a tumor environment, wherein cancer cells uptake the carrier-free nanoparticle and introduction of the carrier-free nanoparticle may inhibit tumor growth. Still, the carrier-free nanoparticle may comprise a erlotinib-curcumin conjugate. Further, the erlotinib-curcumin conjugate comprises a PEG linked erlotinib-curcumin conjugate. Again, the tumor environment may comprise a pancreatic cancer tumor. Yet again, the carrier-free nanoparticle decreases αvβ3 integrin expression and increases PDK4 gene expression. Further yet, the carrier-free nanoparticle may be delivered in a dose of at least 10 mg/kg into a subject. Further, the nanoparticle may be offered at a dose of 1 mg/kg, 2, 3, 4, 5, 6, 7, 8, 9, 10, 15, 20, 25, 30, 35, 40, 45, 50, or 55 mg/kg as well as ranges of these amounts.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present disclosure will be obtained by reference to the following detailed description that sets forth illustrative embodiments, in which the principles of the disclosure may be utilized, and the accompanying drawings of which.

Figure 1:
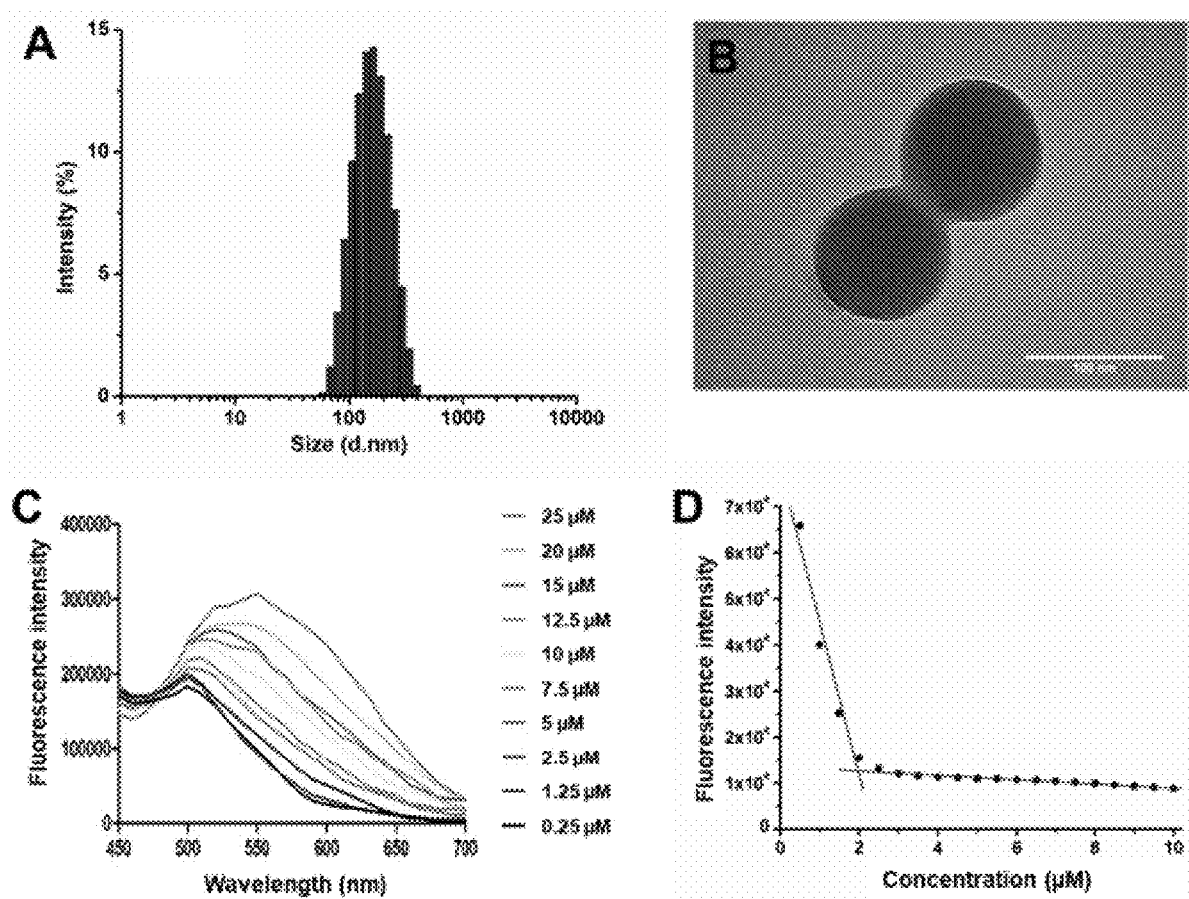
FIG. 1 shows size distribution at (A), TEM image at (B), fluorescence spectra at (C), and CMC determination at (D) of an EPC nanoparticle of the current disclosure.

The figures herein are for illustrative purposes only and are not necessarily drawn to scale.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further embodiment includes from the one particular value and/or to the other particular value. The recitation of numerical ranges by endpoints includes all numbers and fractions subsumed within the respective ranges, as well as the recited endpoints. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than y. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +/−5% or less, +/−1% or less, and +/−0.1% or less of and from the specified value, insofar such variations are appropriate to perform in the disclosure. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such.

It is understood that where "about," "approximate," or "at or about" is used before a quantitative value, the parameter also includes the specific quantitative value itself, unless specifically stated otherwise.

As used herein, a "biological sample" may contain whole cells and/or live cells and/or cell debris. The biological sample may contain (or be derived from) a "bodily fluid". The present disclosure encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, and cell cultures from bodily fluids. Bodily fluids may be obtained from a mammal organism, for example by puncture, or other collecting or sampling procedures.

As used herein, "agent" refers to any substance, compound, molecule, and the like, which can be administered to a subject on a subject to which it is administered to. An agent can be inert. An agent can be an active agent. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

As used herein, "active agent" or "active ingredient" refers to a substance, compound, or molecule, which is biologically active or otherwise that induces a biological or physiological effect on a subject to which it is administered to. In other words, "active agent" or "active ingredient" refers to a component or components of a composition to which the whole or part of the effect of the composition is attributed.

As used herein, "administering" refers to any suitable administration for the agent(s) being delivered and/or subject receiving said agent(s) and can be oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition to the perivascular space and adventitia. For example, a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration routes can be, for instance, auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratym panic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes, which typically depends on the disease to be treated, subject being treated, and/or agent(s) being administered.

As used herein "cancer" can refer to one or more types of cancer including, but not limited to, acute lymphoblastic leukemia, acute myeloid leukemia, adrenocortical carcinoma, Kaposi Sarcoma, AIDS-related lymphoma, primary central nervous system (CNS) lymphoma, anal cancer, appendix cancer, astrocytomas, atypical teratoid/Rhabdoid tumors, basa cell carcinoma of the skin, bile duct cancer, bladder cancer, bone cancer (including but not limited to Ewing Sarcoma, osteosarcomas, and malignant fibrous histiocytoma), brain tumors, breast cancer, bronchial tumors, Burkitt lymphoma, carcinoid tumor, cardiac tumors, germ cell tumors, embryonal tumors, cervical cancer, cholangiocarcinoma, chordoma, chronic lymphocytic leukemia, chronic myelogenous leukemia, chronic myeloproliferative neoplasms, colorectal cancer, craniopharyngioma, cutaneous T-Cell lymphoma, ductal carcinoma in situ, endometrial cancer, ependymoma, esophageal cancer, esthesioneuroblastoma, extracranial germ cell tumor, extragonadal germ cell tumor, eye cancer (including, but not limited to, intraocular melanoma and retinoblastoma), fallopian tube cancer, gallbladder cancer, gastric cancer, gastrointestinal carcinoid tumor, gastrointestinal stromal tumors, central nervous system germ cell tumors, extracranial germ cell tumors, extragonadal germ cell tumors, ovarian germ cell tumors, testicular cancer, gestational trophoblastic disease, Hairy cell leukemia, head and neck cancers, hepatocellular (liver) cancer, Langerhans cell histiocytosis, Hodgkin lymphoma, hypopharyngeal cancer, islet cell tumors, pancreatic neuroendocrine tumors, kidney (renal cell) cancer, laryngeal cancer, leukemia, lip cancer, oral cancer, lung cancer (non-small cell and small cell), lymphoma, melanoma, Merkel cell carcinoma, mesothelioma, metastatic squamous cell neck cancer, midline tract carcinoma with and without NUT gene changes, multiple endocrine neoplasia syndromes, multiple myeloma, plasma cell neoplasms, mycosis fungoides, myelodyspastic syndromes, myelodysplastic/myeloproliferative neoplasms, chronic myelogenous leukemia, nasal cancer, sinus cancer, non-Hodgkin lymphoma, pancreatic cancer, paraganglioma, paranasal sinus cancer, parathyroid cancer, penile cancer, pharyngeal cancer, pheochromocytoma, pituitary cancer, peritoneal cancer, prostate cancer, rectal cancer, Rhabdomyosarcoma, salivary gland cancer, uterine sarcoma, Sezary syndrome, skin cancer, small intestine cancer, large intestine cancer (colon cancer), soft tissue sarcoma, T-cell lymphoma, throat cancer, oropharyngeal cancer, nasopharyngeal cancer, hypoharyngeal cancer, thymoma, thymic carcinoma, thyroid cancer, transitional cell cancer of the renal pelvis and ureter, urethral cancer, uterine cancer, vaginal cancer, cervical cancer, vascular tumors and cancer, vulvar cancer, and Wilms Tumor.

As used herein, "chemotherapeutic agent" or "chemotherapeutic" refers to a therapeutic agent utilized to prevent or treat cancer.

As used herein, "control" can refer to an alternative subject or sample used in an experiment for comparison purpose and included to minimize or distinguish the effect of variables other than an independent variable.

The term "optional" or "optionally" means that the subsequent described event, circumstance, or substituent may or may not occur, and that the description includes instances where the event or circumstance occurs and instances where it does not.

As used herein, "dose," "unit dose," or "dosage" can refer to physically discrete units suitable for use in a subject, each unit containing a predetermined quantity of a pharmaceutical formulation thereof calculated to produce the desired response or responses in association with its administration.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed by the term "subject".

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," can refer to an amount (e.g. mass, volume, dosage, concentration, and/or time period) needed to achieve one or more desired and/or stated result(s). For example, a therapeutically effective amount refers to an amount needed to achieve one or more therapeutic effects.

As used herein, "tangible medium of expression" refers to a medium that is physically tangible or accessible and is not a mere abstract thought or an unrecorded spoken word. "Tangible medium of expression" includes, but is not limited to, words on a cellulosic or plastic material, or data stored in a suitable computer readable memory form. The data can be stored on a unit device, such as a flash memory or CD-ROM or on a server that can be accessed by a user via, e.g. a web interface.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as cancer and/or indirect radiation damage. The effect can be therapeutic in terms of a partial or complete cure of a disease, condition, symptom or adverse effect attributed to the disease, disorder, or condition. The term "treatment" as used herein covers any treatment of cancer and/or indirect radiation damage, in a subject, particularly a human and/or companion animal, and can include any one or more of the following: (a) preventing the disease or damage from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

As used herein, "water-soluble", generally means at least about 10 g of a substance is soluble in 1 L of water, i.e., at neutral pH, at 25° C.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the disclosure. For example, in the appended claims, any of the claimed embodiments can be used in any combination.

All patents, patent applications, published applications, and publications, databases, websites and other published materials cited herein are hereby incorporated by reference to the same extent as though each individual publication, published patent document, or patent application was specifically and individually indicated as being incorporated by reference.

KITS

Any of the compounds and/or formulations described herein can be presented as a combination kit. As used herein, the terms "combination kit" or "kit of parts" refers to the compounds, compositions, formulations, particles, cells and any additional components that are used to package, sell, market, deliver, and/or administer the combination of elements or a single element, such as the active ingredient, contained therein. Such additional components include, but are not limited to, packaging, syringes, blister packages, bottles, and the like. When one or more of the compounds, compositions, formulations, particles, cells, described herein or a combination thereof (e.g., agent(s)) contained in the kit are administered simultaneously, the combination kit can contain the active agent(s) in a single formulation, such as a pharmaceutical formulation, (e.g., a tablet, liquid preparation, dehydrated preparation, etc.) or in separate formulations. When the compounds, compositions, formulations, particles, and cells described herein or a combination thereof and/or kit components are not administered simultaneously, the combination kit can contain each agent or other component in separate pharmaceutical formulations. The separate kit components can be contained in a single package or in separate packages within the kit.

In some embodiments, the combination kit also includes instructions printed on or otherwise contained in a tangible medium of expression. The instructions can provide information regarding the content of the compounds and/or formulations, safety information regarding the content of the compounds and formulations (e.g., pharmaceutical formulations), information regarding the dosages, indications for use, and/or recommended treatment regimen(s) for the compound(s) and/or pharmaceutical formulations contained therein. In some embodiments, the instructions can provide directions and protocols for administering the compounds and/or formulations described herein to a subject in need thereof. In some embodiments, the instructions can provide one or more embodiments of the methods for administration of a pharmaceutical formulation such as any of the methods described in greater detail elsewhere herein.

The current disclosure describes the preparation of a carrier-free nanoparticle and its application. The self-assembled nanoparticle can selectively target EGFR positive tumor and inhibit its growth. Most nanoparticle based drug delivery systems are composed of a carrier and a payload. However, due to the low drug loading content, premature drug release, non-standardized carrier structure, and difficulty in predicating the fate of the carrier, only a few nanomedicines have been approved by FDA.

Erlotinib (compound OSI-774 developed by Genentech, Inc. and OSI Pharmaceuticals, Inc.; available under the trade name TARCEVA) induces dramatic clinical responses in cases of non-small cell lung cancers (NSCLCs) harboring activating mutations in the EGF receptor (EGFR) (1-3), which is targeted by these competitive inhibitors of ATP binding (4, 5). The effectiveness of this tyrosine kinase inhibitor may result both from alterations in the ATP cleft associated with these mutations, which lead to enhanced inhibition of the mutant kinase by these drugs, and from biological dependence of these cancer cells on the increased survival signals transduced by the mutant receptors, a phenomenon described as "oncogene addiction" (6, 7).

The current disclosure provides, in one aspect, a carrier-free nanoparticle based on the self-assembly of curcumin-erlotinib conjugate (EPC) for the treatment of cancer. EPC exhibits stronger cell killing, better anti-migration and anti-invasion effects for BxPC-3 pancreatic cancer cells than the combination of free curcumin and erlotinib. Furthermore, EPC nanoparticles could effectively accumulate in the tumor tissue in a xenograft tumor mouse model. Consequently, EPC effectively reduces the growth of pancreatic tumor and extended the medium survival time.

It was reported that the combination usage of erlotinib (ELT) and curcumin (CCM) could affect the drug resistance signaling pathways through decreasing the αvβ3 integrin and increasing PDK4 gene expression, resulting in higher anticancer effectiveness. In spite of the better performance of the combination therapy compared to individual drugs, the aforementioned limitations of CCM are still unresolved, which restricts its applications in the biomedical field. Herein, is disclosed an ELT and CCM conjugated carrier-free nanoparticle to circumvent the limitations of CCM and enhance the synergistic anticancer effect of the two drugs.

Methods:

Synthesis of PEG Modified Erlotinib (ELT-PEG)

In a 25 mL round-bottom flask equipped with a magnetic stirring bar, ELT (944 mg, 2.4 mmol), azido-PEG3-acid (466 mg, 2.0 mmol), $CuSO_4 \cdot 5H_2O$ (100 mg, 0.4 mmol), and sodium ascorbate (158 mg, 0.8 mmol) were dissolved in 10 mL mixed solvents $DMF/H_2O/t\text{-BuOH}=2/1/2$ under nitrogen atmosphere. The reaction mixture was warmed to 40° C. and stirred for 24 h. Then it was condensed and extracted with dichloromethane (DCM). The organic phase was dried over $Na_2SO_4$ and condensed in vacuum. The crude product was separated by flash column chromatography with silica gel (100 μm) using the gradient elution solvents of methanol and DCM (10/90) to afford ELT-PEG as a light-yellow oil (921 mg, 73.5%). The molecular structure of the product was confirmed by mass spectrometry (MS) and nuclear magnetic resonance spectroscopy (NMR).

Synthesis of PEG Linked Erlotinib-Curcumin Conjugate (EPC)

NHS (115 mg, 1.0 mmol) was added to a 10 mL DMF solution of mixed ELT-PEG (627 mg, 1.0 mmol) and EDC (230 mg, 1.5 mmol) stirred under nitrogen atmosphere for 30 min in a 25 mL round-bottom flask equipped with a magnetic stirring bar. After stirring at room temperature for 1 h, CCM (1.105 g, 3.0 mmol) was added into the reaction mixture and stirred at room temperature overnight. The reaction mixture was condensed under vacuum, and then extracted with DCM/$H_2O$ and washed three times with brine. The organic phase was dried by anhydrous $Na_2SO_4$, filtered, and then evaporated in vacuo. The crude product was separated by flash column chromatography with silica gel (100 μm) using the gradient elution solvents of methanol and DCM (5/95) to afford EPC as an orange solid (520 mg, 53.2%). The chemical structure of EPC was confirmed by MS and NMR results.

Preparation of EPC Nanoparticle

An EPC nanoparticle (NP) was prepared by a one-step nano-precipitation method. The compound EPC was first dissolved in acetone and then added dropwise into deionized water with a syringe pump at 20 mL/h rate under vigorous stirring. Self-assembly of the NP occurred spontaneously. Acetone in the nano-formulation was removed at room temperature under vacuum. The particle size, polydispersity index (PDI), and zeta potential of the NPs were measured by dynamic light scattering (DLS, Zetasizer Nano ZS, Malvern Instruments Ltd, Malvern, UK). The morphology of the NP was observed using a Hitachi HT7800 transmission electron microscopy (TEM, Hitachi High-Technologies Corporation, Tokyo, Japan).

Critical Aggregation Concentration

Critical aggregation concentration (CAC) of EPC was determined by measuring the fluorescence emission of EPC with various concentrations in water. The fluorescence intensity of EPC NP dispersion in deionized water with a series of concentrations (from 0.5 μM to 10 μM) was measured ($\lambda ex$=420 nm, $\lambda em$=530 nm). The CAC value of EPC was calculated according to a plot of relative fluorescence intensity versus concentration.

Cell Culture

Human pancreatic cancer cells, BxPC-3, were cultured in Gibco™ DMEM supplemented with 10% FBS, 100 units/mL penicillin, and 100 μg/mL streptomycin at 37° C. in 75 mL culture flasks under a humidified atmosphere of 5% $CO_2$. Cells were sub-cultured when the cell confluency reached ~80%.

Cellular Uptake

The cellular uptake of EPC was qualitatively examined by confocal laser scanning microscopy (CLSM) with BxPC-3 cells. Cells were seeded in 35 mm 2 Petri dish with a glass window at a density of 200,000 cells/dish for 24 h at 37° C. with 5% $CO_2$. Then cells were washed with PBS (pH 7.4) and incubated with CCM, ELT, or EPC at a concentration of 10 μM for 3 h. Cells without receiving any treatment were utilized as control. All cells were subsequently washed three times with PBS and fixed with paraformaldehyde (4% in PBS) for 10 min at room temperature. Cells were washed with PBS again for three times after the removal of paraformaldehyde, and the nuclei of cells were stained with Hoechst 33342 (final concentration 1 μg/mL) for 10 min. At last, cells were washed three times with PBS and then imaged under a confocal microscope (LSM 700, Carl-Zeiss Inc.).

Flow Cytometry

The uptake of EPC by BxPC-3 cells was further quantitatively determined by flow cytometry. Cells were seeded in 6-well plates at a density of 300,000 cells/well for 24 h at 37° C. with 5% $CO_2$. Then cells were washed with PBS (pH 7.4) and incubated with 10 μM CCM, ELT, or EPC for 3 h. Cells with no incubation were utilized as control. After that, cells were washed with PBS, trypsinized with trypsin-EDTA, and collected through centrifuging at 2000 rpm. Cells were suspended into PBS and then centrifuged for two more times. Finally, collected cells were re-suspended into PBS for analysis. Intracellular fluorescence intensity was quantified by flow cytometer (BD Accuri C6, BD Biosciences).

Cellular Uptake Determination

The intracellular levels of CCM and EPC were determined by fluorescence spectrometer. Cells were seeded in 6-well plates at a density of 700,000 cells/well for 24 h at 37° C. with 5% $CO_2$. Then cells were washed with PBS (pH 7.4) and incubated with 20 μM CCM or EPC for 3 h. Cells with no incubation were utilized as control. After that, cells were washed with PBS, trypsinized with trypsin-EDTA, and collected through centrifuging at 2000 rpm. Then cells were suspended in 1004 ice-cold deionized water and ultrasonicated for 20 min at 4° C. 1004 DMSO was added and the resulted mixture was centrifuged at 10,000 rpm for 10 min. The fluorescence emission of the supernatant was measured ($\lambda ex$=420 nm, $\lambda em$=530 nm).

Cytotoxicity Assay

The anticancer activity of the EPC NP against BxPC-3 cells was evaluated by MTT assay. Cells were seeded in 96-well plates at a density of 5,000 cells/well for 24 h prior to the test at 37° C. with 5% $CO_2$. Then cells were treated with varying concentrations of CCM, ELT, CCM+ELT, or EPC in fresh medium and further incubated for 20 h. In the control group, cells were allowed to grow without any treatment. After that, the medium was replaced with fresh medium containing MTT reagent (final concentration 1 mg/mL) and cells were further incubated for 4 h. The purple MTT crystal was dissolved with MTT stop solution and the optical density at 595 nm was recorded on a microplate reader (ELX808, Bio-Tech Instrument, Inc.).

Wound Healing Assay

BxPC-3 cells were seeded in a 6-well plate at the concentration of 2,000,000 cells/well. When the cell confluency reached almost 100%, the supernatant was aspirated and then the cells were scratched with a yellow pipette tip to generate the wound. After being washed with PBS, the cells were incubated with medium containing 10 μM CCM, ELT, CCM+ELT, or EPC for 24 h. The scratched areas were monitored and photographed with light microscopy.

Transwell Invasion Assay

Cell invasion assay was performed using a 24-well plate with 8 μm pore size Transwell inserts (Costar Corp., Cambridge, MA). Briefly, 50 μL Matrigel was added into each insert and solidified at 37° C. for 30 minutes to generate a thin gel layer. BxPC-3 cells treated with 10 μM CCM, ELT, CCM+ELT, or EPC in 200 μL serum-free medium were transferred into upper chambers at the concentration of 100,000 cells/well. The bottom chambers contained 600 μL complete medium with the same concentration of respective drugs. After incubation at 37° C. for 24 h, cells in the upper chamber were removed, and the invaded cells attached to the underside surface of the membrane were fixed with 4% paraformaldehyde for 30 min and then counted under a light microscope.

Cell Adhesion Assay

Cellular adhesion test was performed in a 24-well plate coated with 0.1 mg/mL Matrigel. In brief, BxPC-3 cells treated with 10 μM CCM, ELT, CCM+ELT, or EPC in 0.5 mL serum-free medium were transferred into each well at the density of 100,000 cells/well. The plate was incubated at 37° C. for 60 min, after which it was washed with PBS to remove unattached cells. Cells attached to Matrigel were fixed with methanol for 15 min and then counted in five random optical fields as determined by light microscopy.

Tumor Spheroid Assay

BxPC-3 cells were seeded in Corning® Ultra-Low Attachment 96-well plate at a density of 50,000 cells/well. Cells were incubated for 5 days to form tumor spheroids. Tumor spheroids were incubated with CCM, ELT, CCM+ELT, or EPC at a concentration of 20 μM for 6 h. Tumor spheroids without any treatment were utilized as a control. Then the tumor spheroids were washed with PBS and imaged with the confocal microscope.

To investigate the cytotoxicity that the EPC NPs exerted to the tumor spheroids, the spheroids were incubated with 20 μM CCM, ELT, CCM+ELT, or EPC for 24 h. Tumor spheroids treated with PBS were utilized as a control. The morphology change of tumor spheroids after the treatments was observed by light microscopy. To visually evaluate the cytotoxicity effect of EPC, red-emissive propidium iodide was used to stain dead cells. The tumor spheroids were stained with propidium iodide (5 μM) for 2 h and then were washed with PBS and imaged with the confocal microscope.

Animal Model

All animal experiments were conducted in accordance with NIH regulations and approved by the Institutional Animal Care and Use Committee of the University of South Carolina. In brief, 2,000,000 BxPC-3 cells suspended in 100111_ DMEM culture medium were inoculated subcutaneously to a female nude mouse (8-10 weeks old, ~20 g, Jackson Laboratories). The tumor volume was measured by a digital caliper and calculated according to the following formula: Tumor volume=0.5×(tumor length)×(tumor width)2. Tumor volumes were monitored every other day. The body weight and signs of pain of the animals were observed throughout the duration of experiments.

In Vivo Biodistribution

Three weeks after the inoculation of BxPC-3 cells, the tumor-bearing mice were administered with CCM and EPC by intravenous injection at a dose of 10 mg/kg equivalent to CCM. PBS (pH 7.4) was used as a control. Mice were sacrificed after 6 h post-injection, and the organs and tumors were collected for imaging. The fluorescence was recorded ex vivo with the IVIS Lumina III whole body imaging system.

Anti-Tumor Efficacy

When the tumor volume of BxPC-3 tumor-bearing mice reached 100 mm$^3$, the mice were randomly assigned into five groups (n=5 for each group) and were intravenously administered with PBS, CCM, ELT, CCM+ELT, or EPC at a dose of 10 mg kg$^{-1}$ equivalent to CCM (10.7 mg/kg equivalent to ELT) twice a week. Tumor volumes (V) and body weight of the mice were measured every other day. The relative tumor volume expressed as V/V$_0$ (V$_0$ is the tumor volume when the treatment was initiated) was used to represent the tumor size change during the treatment process. Mice were sacrificed when the tumor volume reached 2,000 mm 3 or tumor ulceration observed, and the organs and tumors were harvested for further analysis.

FIGURES

Figure 2:
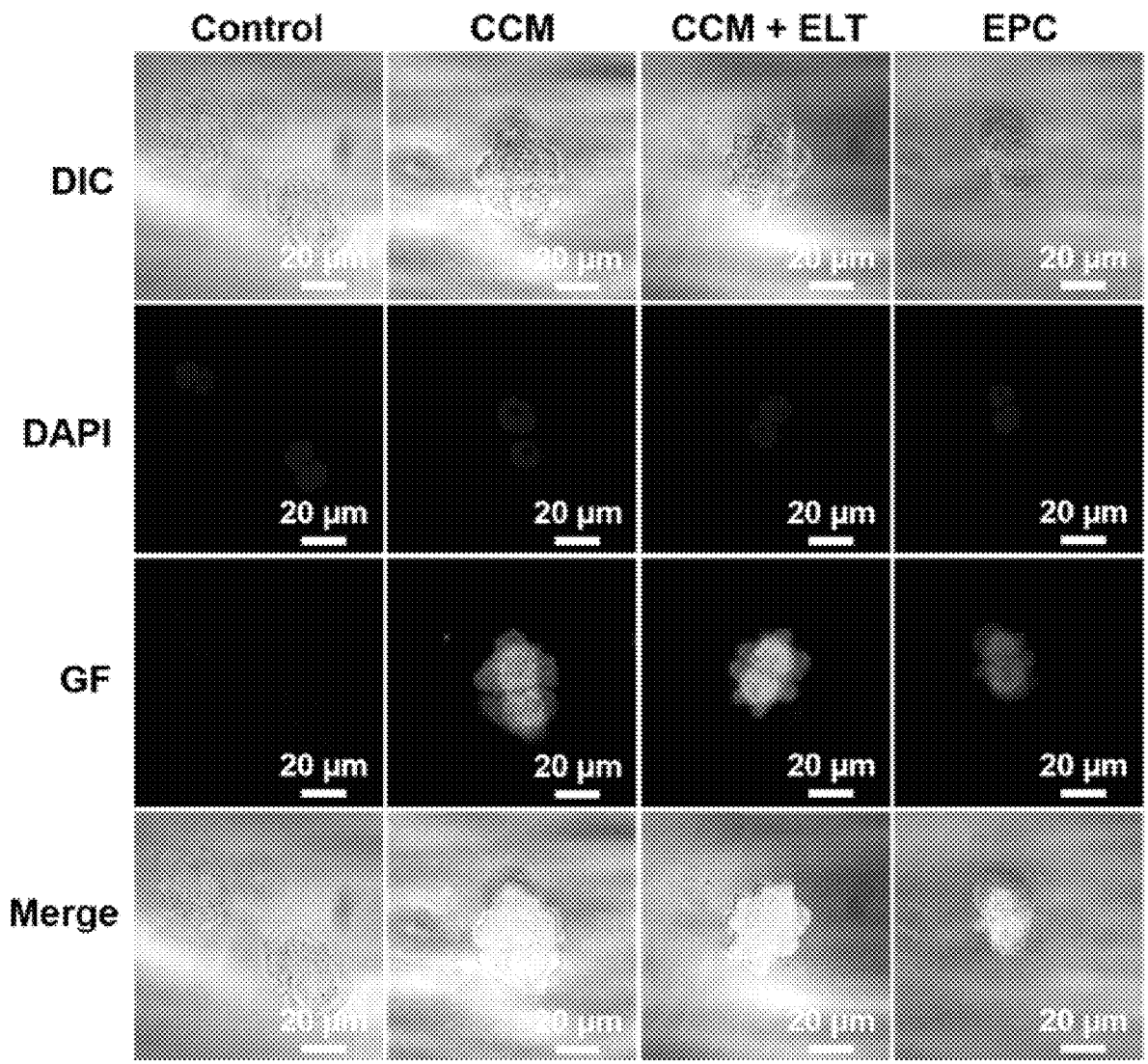
FIG. 2 shows representative CLSM images of BxPC-3 cells after various treatments for 3 h.
Figure 3:
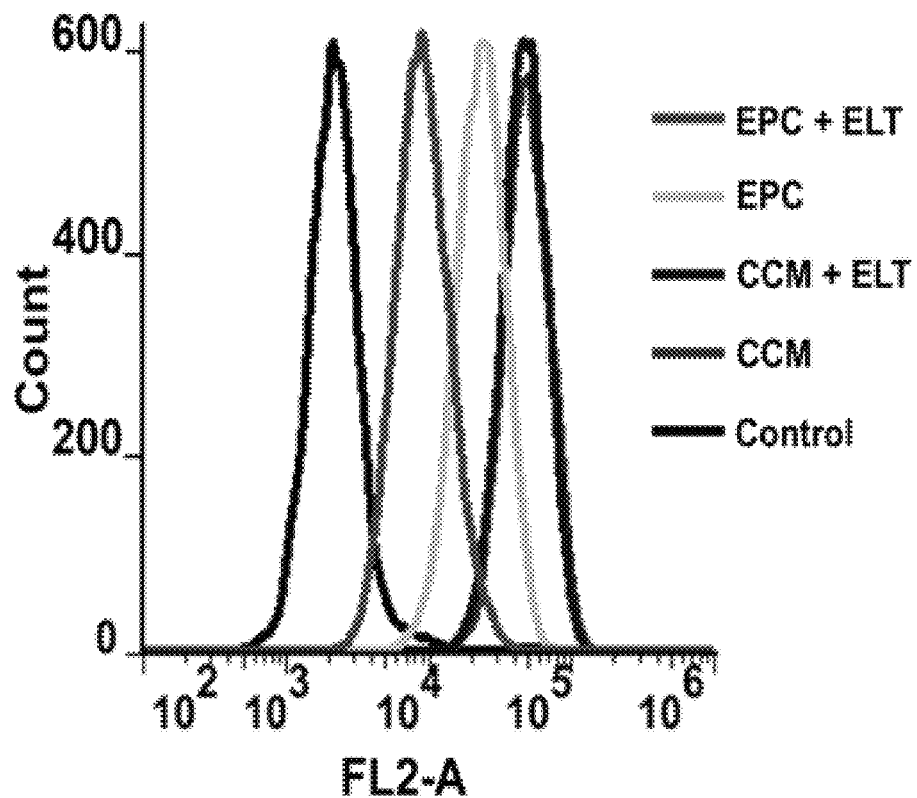
FIG. 3 shows flow cytometry analysis of BxPC-3 cells after various treatments for 3 h.
Figure 4:
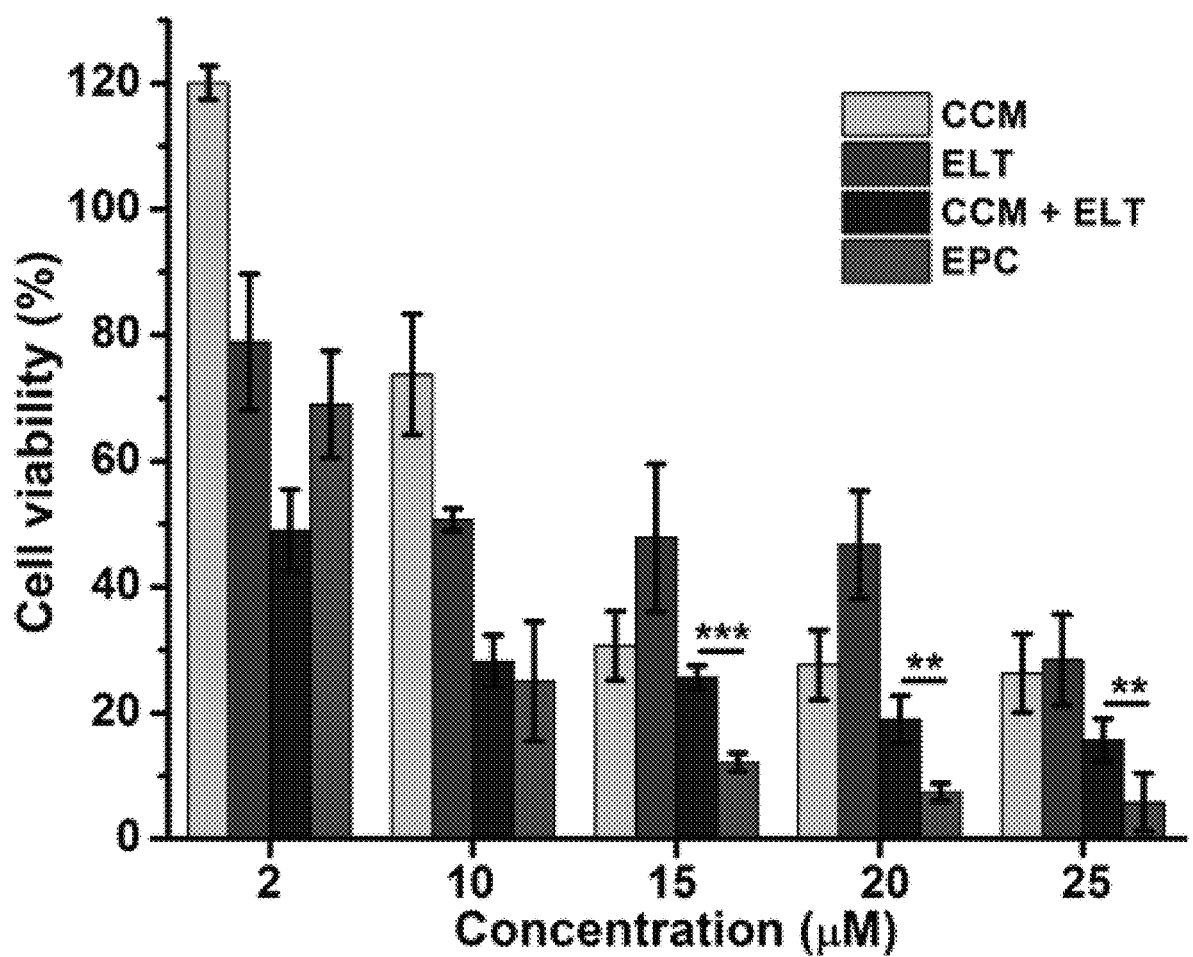
FIG. 4 shows cell viability of BxPC-3 cells after various treatments for 24 h. n=3, *P<0.05; P<0.01; and *P<0.001.
Figure 5:
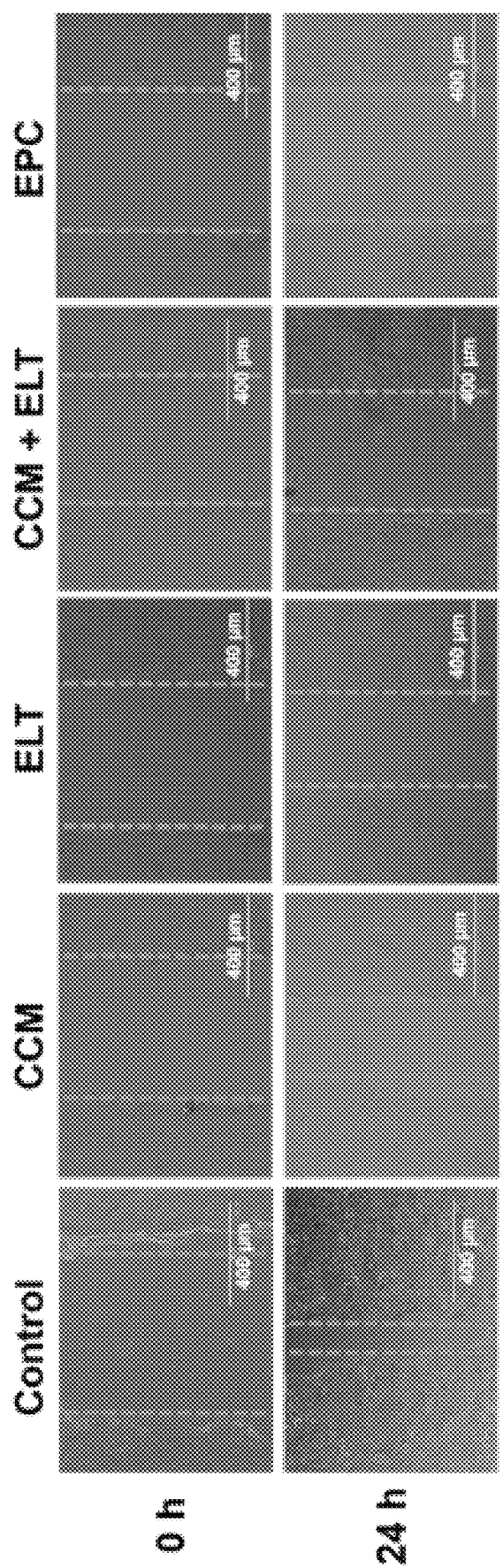
FIG. 5 shows wound healing assay of BxPC-3 cells after treatments with curcumin (CCM), erlotinib (ELT), CCM+ELT, and EPC for 24 h.
Figure 6:
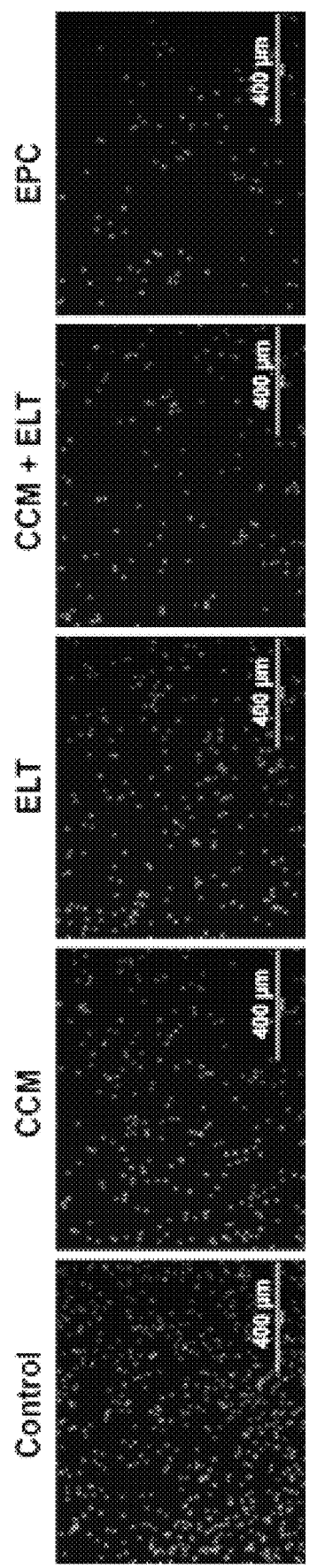
FIG. 6 shows cell adhesion assay of BxPC-3 cells after treatments with CCM, ELT, CCM+ELT, or EPC. n=3, *P<0.05; P<0.01; and *P<0.001.
Figure 7:
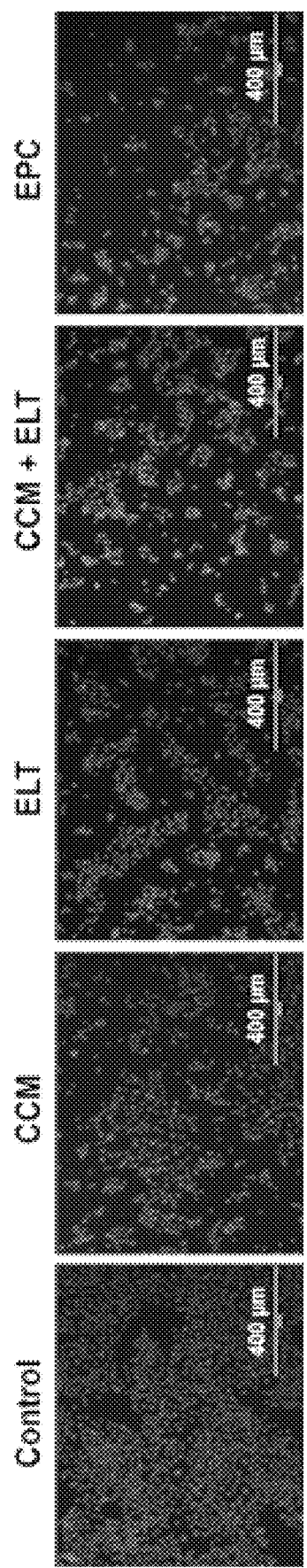
FIG. 7 shows Transwell invasion assay of BxPC-3 cells after various treatments. n=3, *P<0.05; P<0.01; and *P<0.001.
Figure 8:
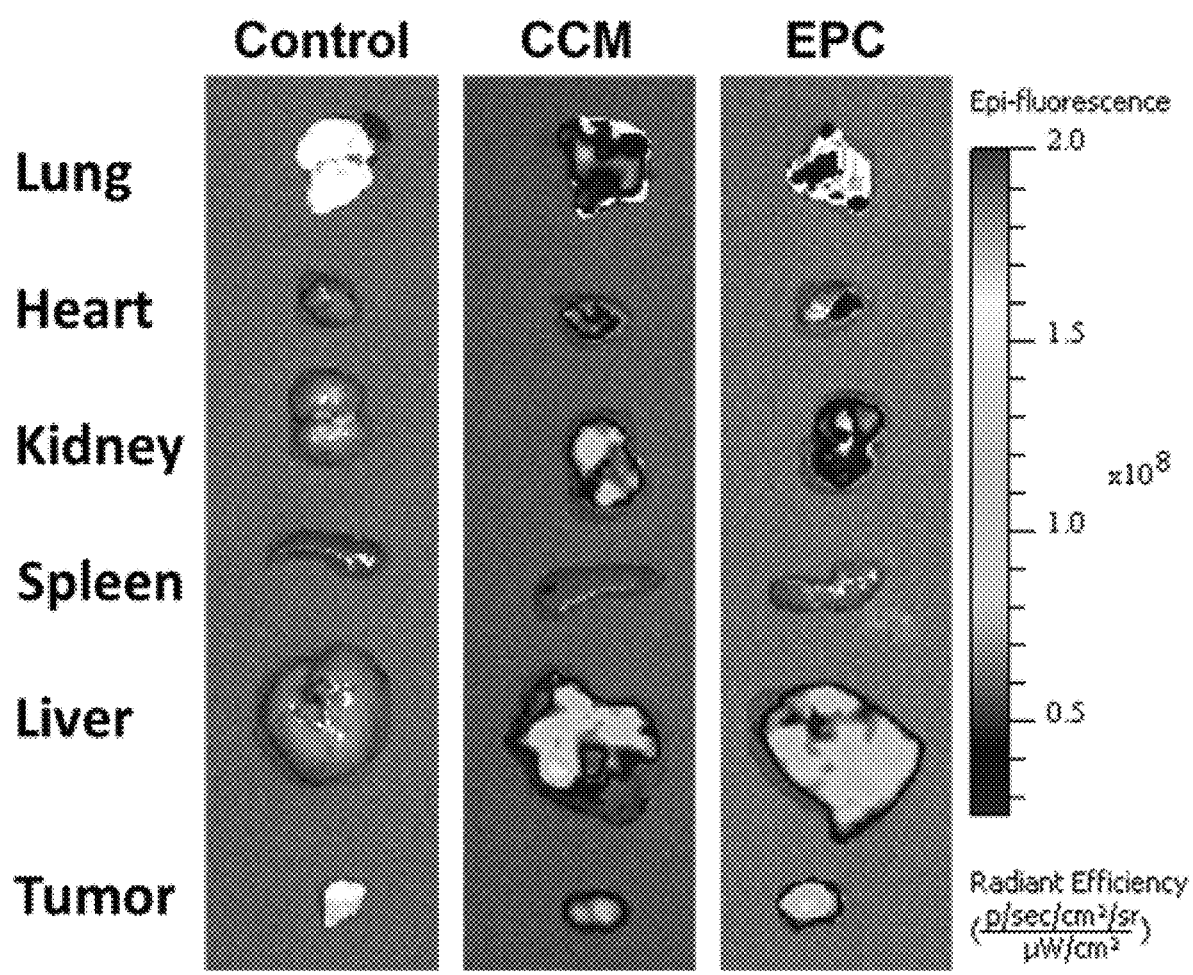
FIG. 8 shows ex vivo biodistribution of CCM and EPC nanoparticle.
Figure 9:
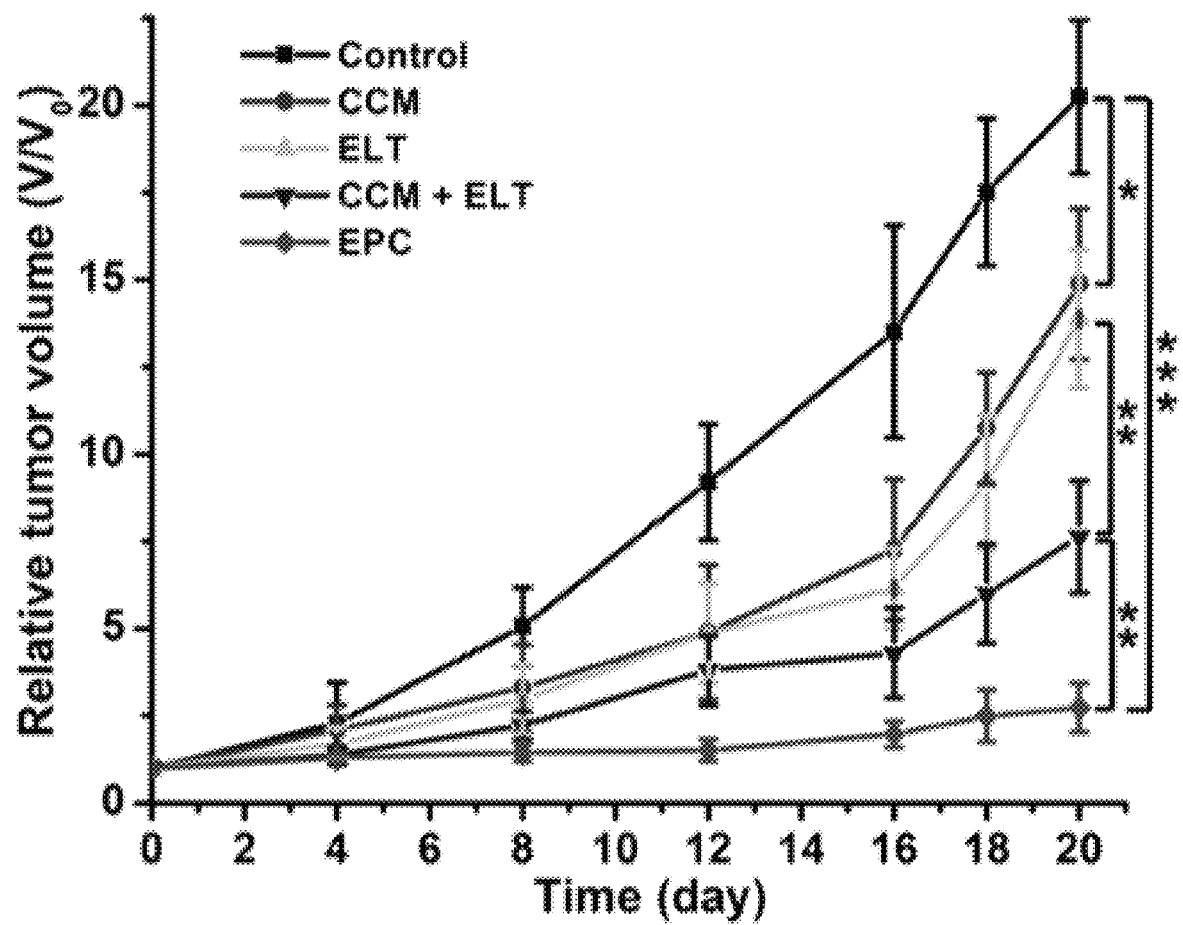
FIG. 9 shows tumor growth profiles of mice treated with different formulations. n=5, *P<0.05; P<0.01; and *P<0.001.
Figure 10:
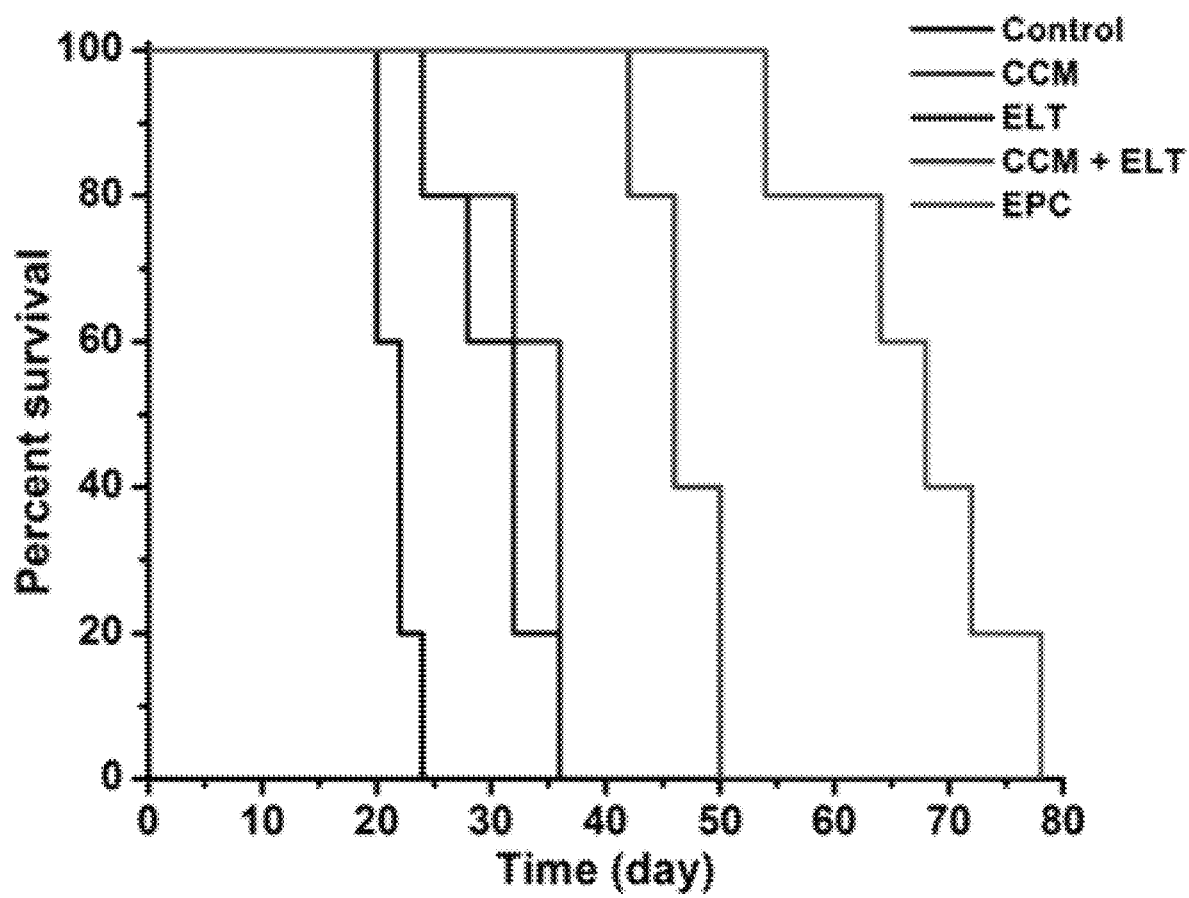
FIG. 10 shows the post-administration survival curve for mice treated with different formulations.
Figure 11:
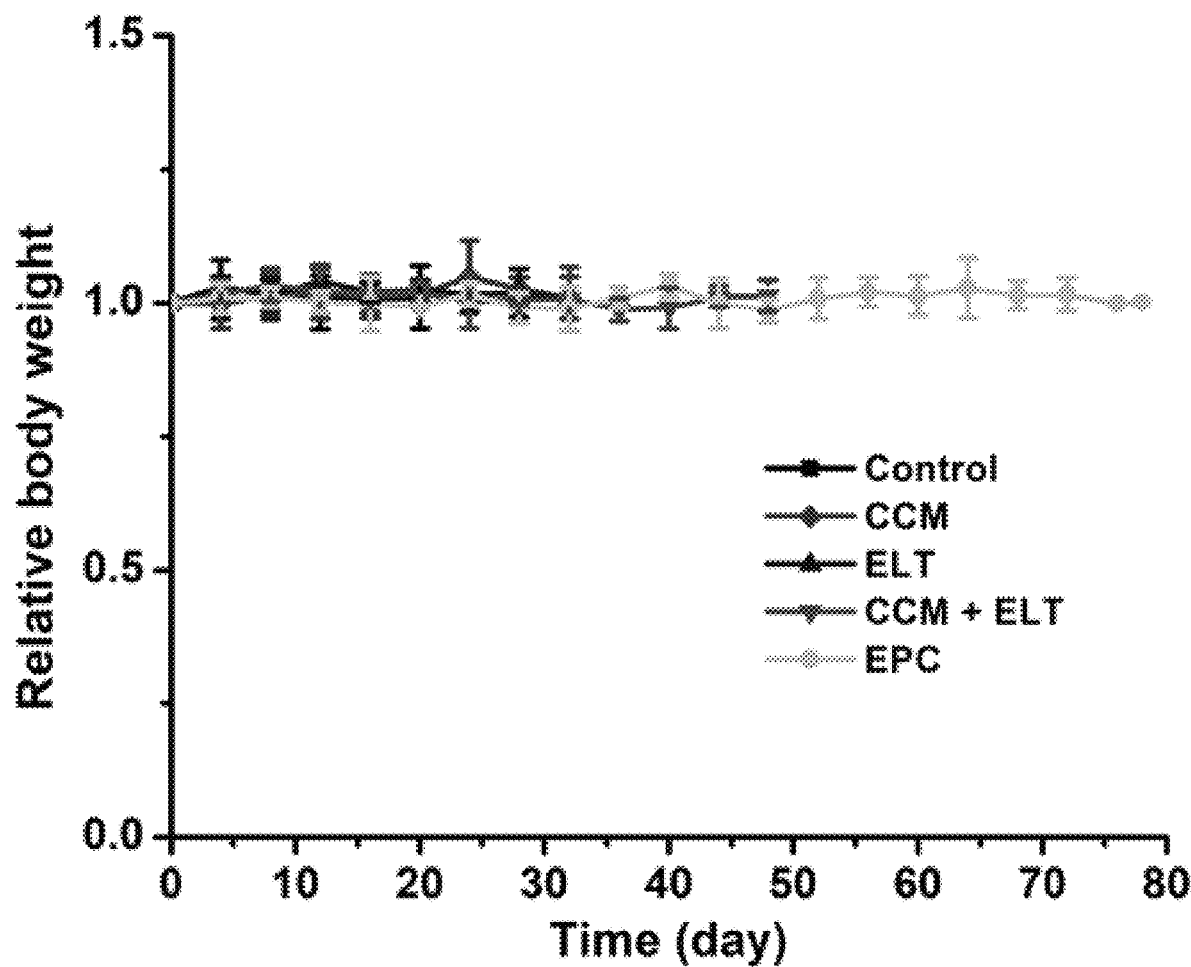
FIG. 11 shows body weight changes of mice receiving different treatments.
Figure 12:
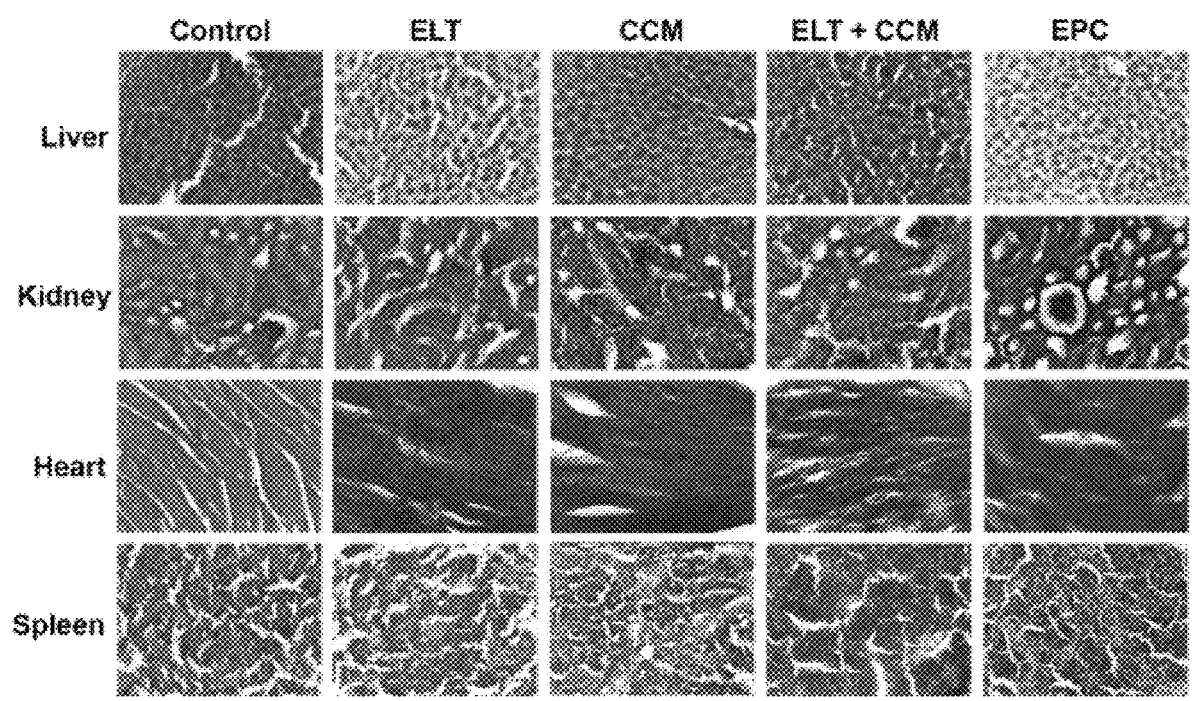
FIG. 12 shows H&E staining of major organs in different groups.

FIG. 1 shows size distribution at (A), TEM image at (B), fluorescence spectra at (C), and CMC determination at (D) of an EPC nanoparticle of the current disclosure. FIG. 2 shows representative CLSM images of BxPC-3 cells after various treatments for 3 h. The green fluorescence (GF channel) is from CCM/EPC and the blue fluorescence (DAPI channel) is from Hoechst 33342. The scale bar is 20 μm. FIG. 3 shows flow cytometry analysis of BxPC-3 cells after various treatments for 3 h. FIG. 4 shows cell viability of BxPC-3 cells after various treatments for 24 h. n=3, *$P<0.05$; $P<0.01$; and *$P<0.001$. FIG. 5 shows wound healing assay of BxPC-3 cells after treatments with CCM, ELT, CCM+ELT, and EPC for 24 h. FIG. 6 shows cell adhesion assay of BxPC-3 cells after treatments with CCM, ELT, CCM+ELT, or EPC. n=3, *$P<0.05$; $P<0.01$; and *$P<0.001$. FIG. 7 shows Transwell invasion assay of BxPC-3 cells after various treatments. n=3, *$P<0.05$; $P<0.01$; and *$P<0.001$. FIG. 8 shows ex vivo biodistribution of CCM and EPC nanoparticle. FIG. 9 shows tumor growth profiles of mice treated with different formulations. n=5, *$P<0.05$; $P<0.01$; and *$P<0.001$. FIG. 10 shows the post-administration survival curve for mice treated with different formulations. FIG. 11 shows body weight changes of mice receiving different treatments. FIG. 12 shows H&E staining of major organs in different groups.

All patents, patent applications, published applications, and publications, databases, websites and other published materials referred to throughout the entire disclosure herein, unless noted otherwise, are incorporated herein by reference in their entirety.

Various modifications and variations of the described methods, pharmaceutical compositions, and kits of the disclosure will be apparent to those skilled in the art without departing from the scope and spirit of the disclosure. Although the disclosure has been described in connection with specific embodiments, it will be understood that it is capable of further modifications and that the disclosure as claimed should not be unduly limited to such specific embodiments. Indeed, various modifications of the described modes for carrying out the disclosure that are obvious to those skilled in the art are intended to be within the scope of the disclosure. This application is intended to cover any variations, uses, or adaptations of the disclosure following, in general, the principles of the disclosure and including such departures from the present disclosure come within known customary practice within the art to which the disclosure pertains and may be applied to the essential features herein set forth.

What is claimed is:

1. A method for reducing the viability of a population of cancer cells, the method comprising delivering a plurality of nanoparticles to the population of cancer cells, each nanoparticle comprising a conjugate, the conjugate comprising erlotinib and curcumin linked with a polyethylene glycol.

2. The method of claim 1, wherein the population of cancer cells comprises EGFR positive cancer cells.

3. The method of claim 2, wherein the EGFR positive cancer cells comprise pancreatic cancer cells.

4. The method of claim 2, wherein the EGFR positive cancer cells comprise human pancreatic cancer cell.

5. The method of claim 1, wherein the population of cancer cells are cells of a subject.

6. The method of claim 5, wherein the population of cancer cells are ex vivo or in vivo cells of the subject.

7. The method of claim 6, wherein the population of cancer cells are in vivo cancer cells, wherein the plurality of nanoparticles are delivered by administering a composition comprising the plurality of nanoparticles to the subject.

8. The method of claim 7, wherein the plurality of nanoparticles are administered to the subject at a dosage of from 1 mg/kg to 55 mg/kg.

9. A method for inhibiting the growth of a tumor, the method comprising: introducing a plurality of nanoparticles to a tumor environment, each nanoparticle comprising a conjugate, the conjugate comprising erlotinib and curcumin linked with a polyethylene glycol.

10. The method of claim 9, wherein the tumor environment comprises a tumor that expresses an EGFR receptor.

11. The method of claim 10, wherein the tumor environment comprises a pancreatic cancer tumor.

12. The method of claim 9, wherein the tumor is an in vivo tumor of the subject.

13. The method of claim 12, wherein the tumor is an in vivo tumor, wherein the plurality of nanoparticles are delivered to the tumor by administering a composition comprising the plurality of nanoparticles to the subject.

14. The method of claim 13, wherein the plurality of nanoparticles are administered to the subject at a dosage of from 1 mg/kg to 55 mg/kg.

* * * * *